United States Patent [19]
Fairhurst et al.

[11] Patent Number: 5,194,250
[45] Date of Patent: Mar. 16, 1993

[54] COMPOSITIONS

[75] Inventors: Edgar Fairhurst; Helen Sayers; Steven Poile, all of Weybridge, England

[73] Assignee: Beecham Group p.l.c., England

[21] Appl. No.: 724,462

[22] Filed: Jun. 26, 1991

Related U.S. Application Data

[63] Continuation of Ser. No. 371,432, Jun. 26, 1989, abandoned.

[30] Foreign Application Priority Data

Jun. 25, 1988 [GB] United Kingdom ............... 8815180

[51] Int. Cl.$^5$ ........................... A61K 7/06; A61K 7/48
[52] U.S. Cl. ...................................... 424/70; 424/401; 514/864; 514/880; 514/770; 252/315.2; 252/315.6
[58] Field of Search .............. 424/47, 65, 70, DIG. 5, 424/401; 252/DIG. 5, 315.2, 315.6; 514/880

[56] References Cited

U.S. PATENT DOCUMENTS

| | | | |
|---|---|---|---|
| 3,833,721 | 9/1974 | Saute et al. | 424/47 |
| 3,903,258 | 9/1975 | Siegal | 424/47 |
| 4,675,177 | 6/1987 | Geary | 424/47 |
| 4,954,532 | 9/1990 | Elliott et al. | 514/864 |

FOREIGN PATENT DOCUMENTS 28471 6/1980 Australia .
1461991 1/1977 United Kingdom .

Primary Examiner—Thurman K. Page
Assistant Examiner—Amy Hulina
Attorney, Agent, or Firm—Rosenman & Colin

[57] ABSTRACT

A skin- or hair-care composition containing silica additionally comprises a $C_{2-4}$ alkyl ester of a di, tri- or tetrabasic carboxylic acid or hydroxy-carboxylic acid (optionally acetylated). The alkyl ester may be dissolved in an aqueous solvent system.

4 Claims, No Drawings

COMPOSITIONS

This application is a continuation of 07/371,432 filed 6-26-89, now abandoned.

This invention relates to improvements in or relating to skin- and hair-care compositions containing silica.

The incorporation of silica into skin- and hair-care compositions is known. For example, EP-A-0 118 180 discloses the use of silanised silica gel as an antiseborrheic agent, and EP-A-0 117 621 discloses its use as a deodorant.

However, a disadvantage of previously proposed compositions is that the level of silica has been limited by its tendency to become visible as an unsightly residue on hair or areas of dry (non-greasy) skin.

It has now surprisingly been found that this problem can be overcome by the incorporation into the composition of an ester of a polycarboxylic acid.

Such esters are commercially available, and some, the α-hydroxy derivatives, have been proposed for use in the treatment of skin disorders such as dandruff. They are non-volatile and have the texture of a light oil. However, they are soluble to varying degrees in aqueous alcohols, and most show significant water solubility. Furthermore, they have been found to have the same refractive index as commercially available silicas. As a result, when the silica particles are coated with one of these esters, during which process any air pockets are automatically excluded, they become transparent. The present invention is based on these findings.

A first aspect of the invention therefore provides a skin- or hair-care composition comprising at least 0.5% w/w silica, a $C_{2-4}$ alkyl ester of a di-, tri- or tetrabasic carboxylic acid or hydroxycarboxylic acid, wherein the hydroxy residue is optionally acetylated, and, optionally, an inert diluent or carrier therefor.

Preferred alkyl esters include ethyl and butyl.

Particular polybasic acids include citric, tartaric and succinic acid.

Advantageously, the ester is selected from triethyl citrate, acetyl triethyl citrate, tributyl citrate, acetyl tributyl citrate, diethyl tartrate and diethyl succinate. Preferably the ester is triethyl citrate or tributyl citrate or their acetylated derivatives.

A particular advantage of the esters of the invention is that, unlike other commonly available oils, they have a significant degree of solubility in aqueous solvent systems. Also, unlike many carboxylic acid esters, such as ethyl lactate, they are resistant to hydrolysis when suspended in water or aqueous alcohols. Thus they can be formulated into a stable non-oily composition.

Thus, a further aspect of the invention provides a skin- or hair-care composition comprising a silica, and an ester as defined above dissolved in an aqueous solvent system.

Typically the aqueous solvent system is an aqueous lower alkanol or water, preferably aqueous ethanol.

Preferably ethanol is included in the composition at from 2% to 80% w/w, more preferably 10% to 70% w/w, especially about 30% w/w in antisebborheic and anti-acne preparations, and about 70% w/w in deodorant preparations. The expression, "% w/w", is used in its conventional sense to means "percent by weight".

On application to the skin or hair, the aqueous solvent system evaporates. Once out of solution, the ester becomes associated with the silica particles and masks them by rendering them transparent as described above. The association is particularly strong in the case of hydrophobic silicas such as silanised silica gel, making it particularly suitable for incorporation into compositions of the type described in EP-A-0 118 180.

Surprisingly, it has been found that the antiseborrheic properties of silanised silica gel remain largely unaffected by adsorption of the esters of the invention in the amounts required to mask the presence of the silica.

As indicated above, the silica in the compositions of the invention is preferably a hydrophobic silica such as silanised silica gel. However, it is envisaged that the improvement of the present invention may be applied to any skin- or hair-care composition containing silica, for example as a microencapsulating agent for other active ingredients, or as a deodorant ingredient in which particulate silica is included to increase the evaporative surface area and rapidly remove sweat.

The discovery on which the present invention is based has been found to apply to a wide range of commercially available hydrophilic and hydrophobic silicas, including silica gels and precipitated silicas such as pyrogenic (fumed) silica; examples include Cab-O-Sil M-5, Sipernat D10, Sipernat D17 and Aerosil R972 (all Trade Marks). Suitably the silica has a mean particle size of 0.1 to 20μ, the particles consisting of aggregates of smaller particles.

Preferably the composition comprises at least 0.5% w/w of the silica, more preferably about 2%. The proportion of silica will not normally exceed about 10% w/w, more preferably about 5% w/w.

The amount of ester will normally be selected to give an ester:silica ratio of at least 1:1, preferably about 2:1. Thus, the composition will typically contain at least 1% w/w, preferably about 4% w/w, ester. In the above-mentioned aqueous compositions of the invention, the amount of ester will not normally exceed the solubility limit thereof, which will obviously vary according to the ester used, the solvent system used, and the other ingredients present, and may be as high as 30% w/w. However, it is normally preferred that the ester be present in an amount of up to 20% w/w, more preferably up to 10% w/w.

% As used herein, 'skin- or hair-care composition' denotes any composition which is to be applied to the skin and/or hair for its beneficial therapeutic and/or cosmetic properties, including organoleptic properties.

Suitably the composition is presented in a conventional skin- or hair-care form, for instance as a roll-on formulation, gel, cream, lotion or stick, and will contain conventional carriers and diluents known to be suitable for each particular presentation.

The compositions may also comprise optional accessory ingredients such as perfume, colouring and preserving agents, keratolytics, antibacterials and antimicrobial agents such as Irgasan or chlorhexidine including its salts such as chlorhexidine gluconate.

Preferably the composition is presented as an aqueous ethanolic gel.

A further aspect of the present invention provides a process for the preparation of a composition of the invention, which process comprises admixing the ingredients thereof in the required proportions.

A still further aspect of the invention provides a method for the therapeutic and/or cosmetic treatment of skin and/or hair, which method comprises applying a composition according to the invention to the skin and/or hair.

The antiseborrheic compositions of the invention are typically applied to the skin, usually the face, on a regular (1-3 times per day) basis. They can be formulated as a leave-on product or as a wipe-on, wipe-off cleansing product which is optionally impregnated into absorbent material for use as swabs.

The following Examples illustrate the invention:

| Ingredient | % w/w |
| --- | --- |
| Example 1 |  |
| Oil-free Gel (for seborrhea) |  |
| Silanised silica gel | 2.0 |
| Triethyl citrate | 4.0 |
| Ethanol | 30.0 |
| *Carbopol 940 | 0.5 |
| Triethanolamine | 1.2 |
| *Nipastat | 0.3 |
| Butylparahydroxybenzoate | 0.02 |
| *Germall 115 | 0.3 |
| Deionised water to | 100 |
| Example 2 |  |
| Antimicrobial Gel (for mild acne) |  |
| Silanised silica gel | 1.0 |
| Triethyl citrate | 2.0 |
| Ethanol | 30.0 |
| Chlorhexidine gluconate | 0.5 |
| *Carbopol 940 | 0.5 |
| Triethanolamine | 1.2 |
| *Nipastat | 0.3 |
| Butylparahydroxybenzoate: | 0.02 |
| *Germall 115 | 0.3 |
| Deionised water to | 100 |
| Example 3 |  |
| Roll-on Lotion (deodorant) |  |
| *Cab-O-Sil M-5 | 1.0 |
| Tributyl Citrate | 3.0 |
| Ethanol | 70.0 |
| Irgasan (Triclosan) | 0.5 |
| *Methocel E4M | 2.0 |
| *Nipastat | 0.3 |
| Butylparahydroxybenzoate | 0.02 |
| *Germall 115 | 0.3 |
| Deionised water to | 100 |
| Example 4 |  |
| Matting Emulsion |  |
| *Arlacel 60 | 1.5 |
| *Tween 60 | 2.0 |
| *Arlacel 165 | 5.0 |
| Tributyl citrate | 8.0 |
| *Cab-O-Sil M-5 | 3.0 |
| *Dimethicone 350 | 2.0 |
| *Nipastat | 0.3 |
| Butylparahydroxybenzoate | 0.02 |
| *Germall 115 | 0.3 |
| Deionised water to | 100 |

*Trade Marks.

We claim:

1. A skin or hair-care composition for the treatment of sebhorrea, comprising from 0.5 to 10% w/w of a silanised silica gel as an anti-sebhorreic agent and from 1 to 20% w/w of a liquid ester selected from the group consisting of triethyl citrate, acetyl triethyl citrate, tributyl citrate, acetyl tributyl citrate, diethyl tartrate and diethyl succinate, dispersed in an aqueous solvent system as carrier.

2. A composition according to claim 1, in which the aqueous solvent system is an aqueous lower alkanol or water.

3. A composition according to claim 1, in which the aqueous solvent system is aqueous ethanol.

4. A composition according to claim 1, in which said ester and silica are in a ratio of about 2:1.

* * * * *